US010618976B2

(12) United States Patent
Weissman et al.

(10) Patent No.: US 10,618,976 B2
(45) Date of Patent: Apr. 14, 2020

(54) SIRP-α AGONIST ANTIBODY

(71) Applicant: The Board of Trustees of the Leland Stanford Junior University, Stanford, CA (US)

(72) Inventors: Irving L. Weissman, Stanford, CA (US); Benson George, Palo Alto, CA (US); Nan Guo Ring, New Haven, CT (US); Aaron Michael Ring, New Haven, CT (US); Jens-Peter Volkmer, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 233 days.

(21) Appl. No.: 15/577,565

(22) PCT Filed: Jun. 8, 2016

(86) PCT No.: PCT/US2016/036520
§ 371 (c)(1),
(2) Date: Nov. 28, 2017

(87) PCT Pub. No.: WO2016/205042
PCT Pub. Date: Dec. 22, 2016

(65) Prior Publication Data
US 2018/0171030 A1 Jun. 21, 2018

Related U.S. Application Data

(60) Provisional application No. 62/180,453, filed on Jun. 16, 2015.

(51) Int. Cl.
*C07K 16/28* (2006.01)
*C07K 16/42* (2006.01)

(52) U.S. Cl.
CPC .......... *C07K 16/42* (2013.01); *C07K 16/2803* (2013.01); *C07K 2317/21* (2013.01); *C07K 2317/565* (2013.01); *C07K 2317/75* (2013.01)

(58) Field of Classification Search
None
See application file for complete search history.

(56) References Cited

U.S. PATENT DOCUMENTS

| 8,728,476 B2* | 5/2014 | van den Berg ...... A61K 39/275 424/153.1 |
| 2003/0059937 A1 | 3/2003 | Ruben et al. |

(Continued)

OTHER PUBLICATIONS

Bio-Rad online catalogue, CD172a|ED9, Retrieved online: <URL: https://www.bio-rad-antibodies.com/monoclonal/rat-cd172a-antibody-ed9-mca620.html?f=purified>. [Retrieved on Sep. 13, 2019] 2019.*

(Continued)

*Primary Examiner* — Claire Kaufman
(74) *Attorney, Agent, or Firm* — Pamela J. Sherwood; Bozicevic, Field & Francis LLP

(57) ABSTRACT

Compositions and methods are provided relating to anti-SIRPα agonist antibodies. The antibodies of the invention bind to human SIRPα, and activate signaling, thereby inhibiting processes mediated by SIRPα, including without limitation phagocytosis. Embodiments of the invention include isolated antibodies and derivatives and fragments thereof, pharmaceutical formulations comprising one or more of the anti-SIRPα agonist antibodies; and cell lines that produce these antibodies.

7 Claims, 7 Drawing Sheets
(7 of 7 Drawing Sheet(s) Filed in Color)
Specification includes a Sequence Listing.

(56) References Cited

U.S. PATENT DOCUMENTS

| | | |
|---|---|---|
| 2009/0234106 A1 | 9/2009 | Han et al. |
| 2009/0318297 A1 | 12/2009 | Cappucilli et al. |
| 2011/0142851 A1 | 6/2011 | Misher et al. |
| 2014/0242095 A1 | 8/2014 | Wang et al. |
| 2014/0271644 A1 | 9/2014 | Scheinberg et al. |

OTHER PUBLICATIONS

Zhao et al., CD47—signal regulatory protein-α (SIRPα) interactions form a barrier for antibody-mediated tumor cell destruction, Proc. Natl. Acad. Sci, USA, 108(45):18342-18347 and S1-3, Nov. 8, 2011.*

Irandoust et al., Engagement of SIRPα inhibits growth and induces proragmed cell death in acute myeloid leukemia cells, PLoS ONE, 8(1):e52143, pp. 1-13, Jan. 8, 2013.*

M2U358_9PROT, "Glutathione synthetase", May 1, 2013 [retrieved online Aug. 10, 2016), http://www.uniprot.org/uniprot/M2U358, sequence nts 232-239.

* cited by examiner

SIRP-α AGONIST ANTIBODY

CROSS-REFERENCE

This application is a 371 application and claims the benefit of PCT Application No. PCT/US2016/036520, filed Jun. 8, 2016, which claims benefit of U.S. Provisional Patent Application Ser. No. 62/180,453 filed Jun. 16, 2015, which applications are incorporated herein by reference in their entirety.

BACKGROUND OF THE INVENTION

Signal regulatory proteins (SIRPs) are immunoglobulin superfamily members, where the human proteins include SIRPα, SIRPβ, and SIRPγ. Expression of SIRPs is largely restricted to leukocytes, where SIRPα and SIRPβ are expressed in myeloid lineages, and SIRPγ is expressed in lymphocytes. The extracellular domains of SIRPs consist of a membrane-distal Ig variable-like (IgV) fold, and two membrane-proximal Ig constant-like (IgC) folds. The ectodomains of the various SIRP family members share a high degree of homology between their respective protein sequences. In contrast, the cytoplasmic signaling elements of different SIRPs differ greatly. For instance, the cytoplasmic tail of SIRPα contains four immunoreceptor tyrosine-based inhibitory motifs, which recruit Src homology 2 phosphatases upon phosphorylation.

The major cellular ligand of SIRPα and SIRPγ is CD47, a ubiquitously expressed transmembrane immunoglobulin superfamily protein. CD47 consists of an extracellular IgV fold, a pentamembrane-spanning transmembrane domain, and a cytoplasmic tail. Binding interactions between SIRPα and CD47 have been implicated in regulating many aspects of leukocyte function, in responses regulated in a bidirectional signaling through both receptors. Specifically, activation of macrophage SIRPα results in inhibition of phagocytosis. For example, the inhibition of phagocytosis by tissue-resident macrophages through SIRPα-CD47 interactions is important for successful engraftment of hematopoietic stem cells.

Activation of phagocytosis in a macrophage in contact with a target cell can be viewed as a balance between signals from activating receptors such as FcγR, CR, or LRP-1, and the inhibitory signal from SIRPα ligated by target cell CD47. In the macrophage, neither signal appears to be dominant, but rather the decision to phagocytose a target host cell is based on an integration of positive prophagocytic signals and inhibitory CD47/SIRPα signaling. The same functional regulation also seems to be operating in DCs and in microglia.

In hemophagocytic lymphohistiocytosis, hematopoietic stem cells are phagocytosed by bone marrow macrophages as a result of systemic inflammation. In this disease, hematopoietic stem cells were found to express reduced levels of CD47, demonstrating that pathological conditions may occur where a combination of inflammatory macrophage activation and reduced expression of CD47 results in a severe loss of critical cell types.

Conversely, tumor cells can increase their CD47 expression levels in order to escape macrophage elimination. Studies have shown that a large number of tumor cells do have elevated levels of CD47. By blocking SIRPα on macrophages, phagocytosis of CD47-high cells can be increased to that seen with CD47-low clones. Thus, blocking the CD47/SIRPα interaction is a powerful tool in the treatment of various tumors.

In view of the importance of the interaction between CD47 and SIRPα, molecular tools for regulating this interaction are of clear clinical and research interest. The present invention provides reagents that agonize SIRPα, thus providing for enhanced signaling in this pathway

SUMMARY OF THE INVENTION

Compositions and methods are provided relating to agonistic monoclonal antibodies that bind to and activate SIRPα. The antibodies of the invention, by activating SIRPα, inhibit phagocytosis of opsonized cells by macrophages, and thus are useful in a variety of methods in which reduced phagocytosis is of interest. Embodiments of the invention include isolated antibodies and derivatives and fragments thereof, pharmaceutical formulations comprising one or more of the SIRPα agonist monoclonal antibodies; and cell lines that produce these monoclonal antibodies. Also provided are CDR amino acid sequences that confer the binding specificity of these monoclonal antibodies. These sequences and the cognate epitopes to which the monoclonal antibodies of the invention bind can be used to identify other antibodies that specifically bind and activate SIRPα. Immunotherapeutic methods for treating of disease associated with undesirable levels of phagocytosis are provided, including without limitation reducing the phagocytosis of red blood cells, reducing the phagocytosis of hematopoietic stem cells; and immunosuppression for the treatment of autoimmune disease or transplant rejection. Therapies of interest may also include therapies with CD47-SIRPα axis blocking agents, e.g. where the SIRPα agonist antibody is available as an antidote to CD47 blocking reagents.

In some embodiments, methods are provided to manipulate phagocytosis of hematopoietic cells, including circulating hematopoietic cells, e.g. bone marrow cells, red blood cells, etc. In some embodiments of the invention the circulating cells are hematopoietic stem cells, or hematopoietic progenitor cells, particularly in a transplantation context, where protection from phagocytosis is desirable. In some such methods, an effective dose of the SIRPα agonist antibody is administered in combination with transplantation of hematopoietic stem cells or progenitors thereof, where the dose of antibody decreases the phagocytosis of the transplanted cells relative to the number of phagocytosed cells in the absence of the antibody. In other, related embodiments, an effective dose of SIRPα agonist antibody is provided to an individual suffering from hemophagocytic lymphohistiocytosis, where the dose is effective to increase the survival of hematopoietic stem cells and progeny derived therefrom.

In some embodiments of the invention the circulating hematopoietic cells are red blood cells. In such embodiments the SIRPα agonist antibody is provided in an effective dose to increase hematocrit of the individual being treated, e.g. for treatment of extravascular hemolytic anemia, treatment of anemia of chronic disease, treatment of thalassemias; and the like. In some embodiments, the administration of the antibody is combined with an agent that increases erythropoiesis, e.g. erythropoietin or an analog or mimetic thereof.

In other embodiments the antibodies of the invention are utilized alone or in combination with immunosuppressants for the treatment of autoimmune disease, for reducing graft rejection, and the like.

The SIRPα agonist antibody may have a heavy chain variable region comprising the amino acid sequence of CDR1 and/or CDR2 and/or CDR3 of the provided human monoclonal human antibodies as provided herein; and/or a light chain variable region comprising the amino acid sequence of CDR1 and/or CDR2 and/or CDR3 of the provided human monoclonal human antibodies as provided herein. In other embodiments, the antibody comprises an amino acid sequence variant of one or more of the CDRs of the provided human antibodies, which variant comprises one or more amino acid insertion(s) within or adjacent to a CDR residue and/or deletion(s) within or adjacent to a CDR residue and/or substitution(s) of CDR residue(s) (with substitution(s) being the preferred type of amino acid alteration for generating such variants). Such variants will normally having a binding affinity of at least about $10^8$, and will bind to the same epitope as an antibody having the amino acid sequence of P362 antibody, as described herein.

Various forms of the antibodies are contemplated herein. For example, the SIRPα agonist antibody may be a full length antibody, e.g. having a human immunoglobulin constant region of any isotype, e.g. IgG1, IgG2a, IgG2b, IgG3, IgG4, IgA, etc. or an antibody fragment, e.g. a $F(ab')_2$ fragment, and F(ab) fragment, etc. Furthermore, the antibody may be labeled with a detectable label, immobilized on a solid phase and/or conjugated with a heterologous compound.

The invention further provides: isolated nucleic acid encoding the antibodies and variants; a vector comprising that nucleic acid, optionally operably linked to control sequences recognized by a host cell transformed with the vector; a host cell comprising that vector; a process for producing the antibody comprising culturing the host cell so that the nucleic acid is expressed and, optionally, recovering the antibody from the host cell culture (e.g. from the host cell culture medium). The invention also provides a composition comprising one or more of the human SIRPα agonist antibodies and a pharmaceutically acceptable carrier or diluent. This composition for therapeutic use is sterile and may be lyophilized, e.g. being provided as a pre-pack in a unit dose with diluent and delivery device, e.g. inhaler, syringe, etc.

Other aspects and features will be readily apparent to the ordinarily skilled artisan upon reading the present disclosure.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1A. Dose response curve of P362 hIgG4 blocking of recombinant human CD47 from binding to human SIRPα displayed on yeast. FIG. 1B. Dose response curve of P362 hIgG4 binding to SIRPα on primary human macrophages.

FIG. 3A P362 hIgG4 significantly decreased cetuximab-induced phagocytosis of DLD-1 colon cancer cells. FIG. 3B P362 hIgG4 also significantly decreased rituximab-induced phagocytosis of Raji lymphoma cells.

FIG. 5. P362 Protects Against Anti-CD235a Mediated Erythrophagocytosis. Dose response curve of phagocytosis of RBCs, where increasing concentrations of P362 hIgG4 was titrated in the presence of a fixed dose of anti-CD235a. P362 hIgG4 significantly inhibited the clearance of RBCs by primary human macrophages when opsonized by anti-CD235a.

DETAILED DESCRIPTION OF THE EMBODIMENTS

Figure 1B:
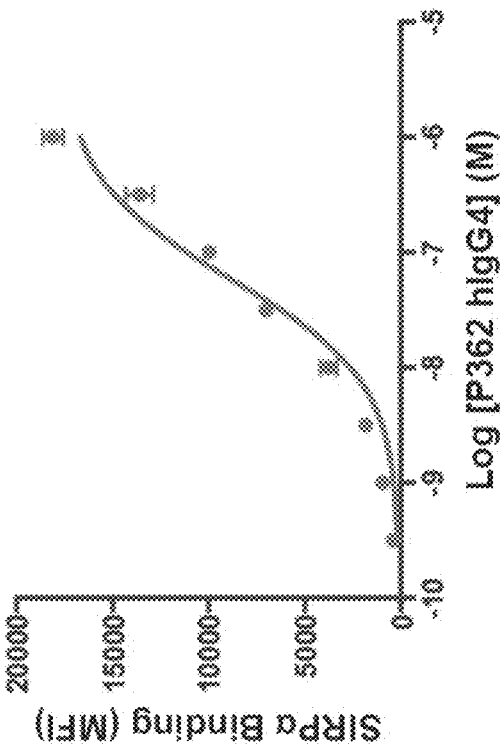
FIG. 1A-1B. P362: A Fully-Human Anti-SIRPα Agonistic Antibody.

It is to be understood that the invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the polypeptide" includes reference to one or more polypeptides and equivalents thereof known to those skilled in the art, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

By "manipulating phagocytosis" is meant an up-regulation or a down-regulation in phagocytosis by at least about 10%, or up to 20%, or 50%, or 70% or 80% or up to about 90% compared to level of phagocytosis observed in absence of intervention. Thus in the context of decreasing phagocytosis, e.g. of circulating hematopoietic cells, including without limitation in a transplantation context or a hemophagocytic lymphohistiocytosis; phagocytosis of erythrocytes, etc., manipulating phagocytosis means a down-regulation in phagocytosis by at least about 10%, of up to about 20%, of up to about 50%, of up to about 70%, of up to about 80%, of up to about 90% compared to the level of phagocytosis observed in absence of intervention. The cell of interest targeted for protection from phagocytosis may have increased expression of CD47; and/or increased levels of opsonization, relative to a normal counterpart of the targeted cell.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system. In embodiments of the present invention, and effective dose is the dose that provides for increased survival of the targeted cell, e.g. an increase in the body of at least about 5%, at least about 10%, at least about 15%, at least about 20%, at least about 25%, at least about 30%, at least about 35%, at least about 40%, at least about 45%, at least about 50%, at least about 75%, at least about 80%, at least about 90%, at least about 95%, at least about 1-fold, at least about 2-fold, at least about 3-fold, at least about 4-fold, at least about 5-fold, or more.

Effective dosages may be estimated initially from in vitro assays. For example, an initial dosage for use in animals may be formulated to achieve a circulating blood or serum concentration of active compound that is at or above an $10_{50}$ of the particular compound as measured in an in vitro assay. Calculating dosages to achieve such circulating blood or scrum concentrations, taking into account the bioavailability of the particular active agent, is well within the capabilities of skilled artisans. For guidance, the reader is referred to Fingl & Woodbury, "General Principles," In: Goodman and Gilman's The Pharmaceutical Basis of Therapeutics, Chapter 1, pp. 1-46, latest edition, Pergamagon Press, which is hereby incorporated by reference in its entirety, and the references cited therein.

Reference herein to "treatment" and "prophylaxis" is to be considered in its broadest context. The term "treatment" does not necessarily imply that a subject is treated until total recovery. Similarly, "prophylaxis" does not necessarily mean that the subject will not eventually contract a disease condition. Accordingly, treatment and prophylaxis can include amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition. Treating or treatment of a disease or condition with oxidative and/or immunomodulatory agents includes: (1) preventing or reducing the risk of developing the disease, i.e., causing the clinical symptoms of the disease not to develop in a subject that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms. In some embodiments, treatment may be understood to not include prevention. The term "modulate" can refer to the treating, prevention, suppression, enhancement or induction of a function or condition. For example, compounds can modulate macrophage activation by enhancing macrophage activation or inhibiting macrophage activation. In some embodiments, the term "modulate" may be understood to not include prevention of a function or condition.

"Polypeptide" and "protein" as used interchangeably herein, can encompass peptides and oligopeptides. Where "polypeptide" is recited herein to refer to an amino acid sequence of a naturally-occurring protein molecule, "polypeptide" and like terms are not necessarily limited to the amino acid sequence to the complete, native amino acid sequence associated with the recited protein molecule, but instead can encompass biologically active variants or fragments, including polypeptides having substantial sequence similarity or sequence identify relative to the amino acid sequences provided herein. In general, fragments or variants retain a biological activity of the parent polypeptide from which their sequence is derived.

As used herein, "polypeptide" refers to an amino acid sequence of a recombinant or non-recombinant polypeptide having an amino acid sequence of i) a native polypeptide, ii) a biologically active fragment of an polypeptide, or iii) a biologically active variant of an polypeptide. Polypeptides suitable for use can be obtained from any species, e.g., mammalian or non-mammalian (e.g., reptiles, amphibians, avian (e.g., chicken)), particularly mammalian, including human, rodent (e.g., murine or rat), bovine, ovine, porcine, murine, or equine, particularly rat or human, from any source whether natural, synthetic, semi-synthetic or recombinant. In general, polypeptides comprising a sequence of a human polypeptide are of particular interest.

The term "derived from" indicates molecule that is obtained directly from the indicated source (e.g., when a protein directly purified from a cell, the protein is "derived from" the cell) or information is obtained from the source, e.g. nucleotide or amino acid sequence, from which the molecule can be synthesized from materials other than the source of information.

The term "isolated" indicates that the recited material (e.g., polypeptide, nucleic acid, etc.) is substantially separated from, or enriched relative to, other materials with which it occurs in nature (e.g., in a cell). A material (e.g., polypeptide, nucleic acid, etc.) that is isolated constitutes at least about 0.1%, at least about 0.5%, at least about 1% or at least about 5% by weight of the total material of the same type (e.g., total protein, total nucleic acid) in a given sample.

The terms "subject" and "patient" are used interchangeably herein to mean a member or members of any mammalian or non-mammalian species that may have a need for the pharmaceutical methods, compositions and treatments described herein. Subjects and patients thus include, without limitation, primate (including humans), canine, feline, ungulate (e.g., equine, bovine, swine (e.g., pig)), avian, and other subjects. Humans and non-human animals having commercial importance (e.g., livestock and domesticated animals) are of particular interest.

"Mammal" means a member or members of any mammalian species, and includes, by way of example, canines; felines; equines; bovines; ovines; rodentia, etc. and primates, particularly humans. Non-human animal models, particularly mammals, e.g. primate, murine, lagomorpha, etc. may be used for experimental investigations.

The term "unit dosage form," as used herein, refers to physically discrete units suitable as unitary dosages for human and animal subjects, each unit containing a predetermined quantity of compounds calculated in an amount sufficient to produce the desired effect in association with a pharmaceutically acceptable diluent, carrier or vehicle. The specifications for the unit dosage forms depend on the particular compound employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and is usually free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., J. Mol. Biol. 186:651 (1985); Novotny and Haber, Proc. Natl. Acad. Sci. U.S.A. 82:4592 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species (scFv), one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. For a review of scFv see Pluckthun, in The Pharmacology of Monoclonal Antibodies, vol. 113, Rosenburg and Moore eds., Springer-Verlag, New York, pp. 269-315 (1994).

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

There are five major classes of immunoglobulins: IgA, IgD, IgE, IgG, and IgM, and several of these can be further divided into subclasses (isotypes), e.g., IgG$_1$, IgG$_2$, IgG$_3$, IgG$_4$, IgA$_1$, IgA$_2$. Included in the constant regions of interest are human IgG4 constant regions with the amino acid substitution S241P (see, for example, Angal et al. (1993) Mol Immunol. 30(1):105-8. The heavy-chain constant domains that correspond to the different classes of immunoglobulins are called $\alpha$, $\delta$, $\epsilon$, $\gamma$, and $\mu$ respectively. The subunit structures and three-dimensional configurations of different classes of immunoglobulins are well known.

The term "human antibody" includes antibodies having variable and constant regions (if present) of human germline immunoglobulin sequences. Human antibodies of the invention also include amino acid residues not encoded by human germline immunoglobulin sequences (e.g., mutations introduced by random or site-specific mutagenesis in vitro or by somatic mutation in vivo). However, the term "human antibody" does not include antibodies in which CDR sequences derived from the germline of another mammalian species, such as a mouse, have been grafted onto human framework sequences (i.e., humanized antibodies).

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

Unless specifically indicated to the contrary, the term "conjugate" as described and claimed herein is defined as a heterogeneous molecule formed by the covalent attachment of one or more antibody fragment(s) to one or more polymer molecule(s), wherein the heterogeneous molecule is water soluble, i.e. soluble in physiological fluids such as blood, and wherein the heterogeneous molecule is free of any structured aggregate. A conjugate of interest is PEG. In the context of the foregoing definition, the term "structured aggregate" refers to (1) any aggregate of molecules in aqueous solution having a spheroid or spheroid shell structure, such that the heterogeneous molecule is not in a micelle or other emulsion structure, and is not anchored to a lipid bilayer, vesicle or liposome; and (2) any aggregate of molecules in solid or insolubilized form, such as a chromatography bead matrix, that does not release the heterogeneous molecule into solution upon contact with an aqueous phase. Accordingly, the term "conjugate" as defined herein encompasses the aforementioned heterogeneous molecule in a precipitate, sediment, bioerodible matrix or other solid capable of releasing the heterogeneous molecule into aqueous solution upon hydration of the solid.

Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgG, IgE and IgM, bi- or multi-specific antibodies (e.g., Zybodies®, etc), single chain Fvs, polypeptide-Fc fusions, Fabs, cameloid antibodies, masked antibodies (e.g., Probodies®), Small Modular ImmunoPharmaceuticals ("SMIPs™"), single chain or Tandem diabodies (TandAb®), VHHs, Anticalins®, Nanobodies®, minibodies, BiTE®s, ankyrin repeat proteins or DARPINs®, Avimers®, a DART, a TCR-like antibody, Adnectins®, Affilins®, Trans-bodies®, Affibodies®, a TrimerX®, MicroProteins, Fynomers®, Centyrins®, and a KALBITOR®. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.]

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Each mAb is directed against a single determinant on the antigen. In addition to their specificity, the monoclonal antibodies are advantageous in that they can be synthesized by cell culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made in an immortalized B cell or hybridoma thereof, may be made by recombinant DNA methods, including without limitation yeast display.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 75% by weight of antibody as determined by the Lowry method, and most preferably more than 80%, 90% or 99% by weight, or (2) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g. an affinity chromatography column). This term also includes a discontinuous solid phase of discrete particles, such as those described in U.S. Pat. No. 4,275,149.

Other definitions of terms appear throughout the specification.

Antibody Compositions

Compositions and methods are provided relating to SIRPα agonist antibodies. The antibodies of the invention bind to and activate SIRPα signaling. SIRPα provides an inhibitory signal, and thus activation of SIRPα decreases phagocytosis mediated by cells, e.g. macrophages, that express SIRPα. Embodiments of the invention include isolated antibodies and derivatives and fragments thereof, pharmaceutical formulations comprising one or more of the antibodies; cell lines that produce these monoclonal antibodies. In some embodiments the antibodies are monoclonal antibodies. In some embodiments the antibodies are human antibodies. In some embodiments the antibodies comprise a human constant region, including without limitation IgG constant regions, e.g. $IgG_1$, $IgG_{2a}$, $IgG_{2b}$, $IgG_3$, $IgG_4$, etc.

In one aspect, the present invention is directed to combinatorially derived human monoclonal antibodies that are specifically reactive with and activate SIRPα, and cell lines which produce such antibodies. Antibodies of interest include these provided combinations, as well as fusions of the variable regions to appropriate constant regions or fragments of constant regions, e.g. to generate F(ab)' antibodies. Variable regions of interest include at least one CDR sequence, where a CDR may be 3, 4, 5, 6, 7, 8, 9, 10, 11, 12 or more amino acids. Alternatively, antibodies of interest include a pair of variable regions as set forth in SEQ ID NO:1 and 2. In other embodiments, one antibody chain can comprise the CDR sequence set forth in SEQ ID NO:3-5. Such an antibody chain may be combined with an antibody chain comprising the CDR sequences set forth in SEQ ID NO:6-8.

In some embodiments one variable region of the antibody comprises the sequence:

(SEQ ID NO: 1)
QVQLVESEGGLVQPGGSLRLSCAASG<u>FTFSSYEMN</u>WVRQAPGKGLE
<u>WVSYISSSGSTIYY</u>ADSVKGRFTISRDNAKNSLYLQMNSLRAEDTAVY
YCA<u>REAKGYYYGMDV</u>WGQGTTVTVSS.

In some embodiments one variable region of the antibody comprises the sequence:

(SEQ ID NO: 2)
QPVLTQSPSVSVSPGQTASITCSGD<u>KLGDTYAC</u>WYQQKPGQSPV<u>LVIYQ
DTKRPS</u>GIPERFSGSNSGNTATLTISGTQAMDEADYYC<u>QAWDSSTV</u>VFGG
GTKLTVL.

In some embodiments, an antibody variable region comprises one or more of the CDR regions set forth in SEQ ID NO:3, FTFSSYEMN; SEQ ID NO:4, WVSYISSSGSTIYY, and SEQ ID NO:5, REAKGYYYGMDV. In some embodiments an antibody variable region comprises one or more of the CDR regions set forth in SEQ ID NO:6, KLGDTYAC; SEQ ID NO:7, LVIYQDTKRPS and SEQ ID NO:8, QAWDSSTV (88-95).

In some embodiments, a CDR set comprises a heavy and light chain comprising, respectively, the CDR sequences set forth in SEQ ID NO:3-5 and SEQ ID NO:6-8. One or more residues of a CDR may be altered to modify binding to achieve a more favored on-rate of binding, a more favored off-rate of binding, or both, such that an optimized binding constant is achieved. Affinity maturation techniques are well known in the art and can be used to alter the CDR region(s), followed by screening of the resultant binding molecules for the desired change in binding. In addition to, or instead of, modifications within the CDRs, modifications can also be made within one or more of the framework regions, FRI, FR2, FR3 and FR4, of the heavy and/or the light chain variable regions of a human antibody, so long as these modifications do not eliminate the binding affinity of the human antibody.

In general, the framework regions of human antibodies are usually substantially identical, and more usually, identical to the framework regions of the human germline sequences from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting human immunoglobulin. Thus, in one embodiment the variable framework region of the human antibody shares at least 85% sequence identity to a human germline variable framework region sequence or consensus of such sequences. In another embodiment, the variable framework region of the human antibody shares at least 90%, 95%, 96%, 97%, 98% or 99% sequence identity to a human germline variable framework region sequence or consensus of such sequences.

In some embodiments an antibody of interest has a contiguous sequence of at least about 10 amino acids as set forth in any one of SEQ ID NO:1 or SEQ ID NO:2, at least about 15 amino acids, at least about 20 amino acids, at least about 25 amino acids, at least about 30 amino acids, up to the complete provided variable region. Polypeptides of interest also include variable regions sequences that differ by up to one, up to two, up to 3, up to 4, up to 5, up to 6 or more amino acids as compared to the amino acids sequence set forth in any one of SEQ ID NO:1 or SEQ ID NO:2. In other embodiments a polypeptide of interest is at least about 80%, at least about 85%, at least about 90%, at least about 95%, at least about 99% identical to the amino acid sequence set forth in any one of SEQ ID NO:1 or SEQ ID NO:2.

The isolation of cells producing monoclonal antibodies of the invention can be accomplished using routine screening techniques, which permit determination of the elementary reaction pattern of the monoclonal antibody of interest. Thus, if a human monoclonal antibody being tested binds to the cognate epitope of one of the provided antibodies, i.e. cross-blocks, and activates SIRPα, then the human monoclonal antibody being tested and the human monoclonal antibody exemplified herein are equivalent.

It is also possible to determine, without undue experimentation, if a monoclonal antibody has the same specificity as a monoclonal antibody of the invention by ascertaining whether the former prevents the latter from binding to or activating SIRPα. If the monoclonal antibody being tested competes with the monoclonal antibody of the invention, as shown by a decrease in binding by the monoclonal antibody of the invention, then the two monoclonal antibodies bind to the same, or a closely related, epitope. Still another way to determine whether a monoclonal antibody has the specificity of a monoclonal antibody of the invention is to pre-incubate the monoclonal antibody of the invention with a cell expressing SIRPα, and then add the monoclonal antibody being tested to determine if the monoclonal antibody being tested is inhibited in its ability to bind SIRPα. If the monoclonal antibody being tested is inhibited then, in all likelihood, it has the same, or functionally equivalent, epitopic specificity as the monoclonal antibody of the invention.

In addition to Fabs, smaller antibody fragments and epitope-binding peptides having binding specificity for at least one epitope of SIRPα are also contemplated by the present invention. For example, single chain antibodies can be constructed according to the method of U.S. Pat. No. 4,946,778 to Ladner et al, which is incorporated herein by reference in its entirety. Single chain antibodies comprise the variable regions of the light and heavy chains joined by a flexible linker moiety. Yet smaller is the antibody fragment known as the single domain antibody, which comprises an isolate VH single domain. Techniques for obtaining a single domain antibody with at least some of the binding specificity of the intact antibody from which they are derived are known in the art. For instance, Ward, et al. in "Binding Activities of a Repertoire of Single Immunoglobulin Variable Domains Secreted from *Escherichia coli*," Nature 341: 644-646, disclose a method for screening to obtain an antibody heavy chain variable region (H single domain antibody) with sufficient affinity for its target epitope to bind thereto in isolate form.

Methods of Use

In some embodiments, methods are provided to enhance transplantation by reducing phagocytosis of transplanted cells. In some embodiments, the transplanted cells are hematopoietic progenitor cells. In some such embodiments, the transplanted cells comprise hematopoietic stem cells. Hematopoietic stem or progenitor cells are protected from phagocytosis when in circulation by providing a recipient with an effective dose of an agonist antibody of the invention. The antibodies of the present invention are useful in such a context as an adjunct to the introduction of the hematopoietic cells.

Hematopoietic stem cell transplantation (HCT) is the transplantation of multipotent hematopoietic stem cells, usually derived from bone marrow, peripheral blood, or umbilical cord blood. Where the donor is deceased, hematopoietic cells may be obtained from bone marrow, e.g. vertebrae, pelvic bone, etc. Where the donor is a living donor, hematopoietic cells may be mobilized, e.g. with G-CSF, and collected by apheresis or similar methods. Alternatively, cells may be obtained from bone marrow, e.g. pelvic bone, etc.

Hematopoietic cells can be frozen (cryopreserved) for prolonged periods without damaging too many cells. To cryopreserve HSC, a preservative, DMSO, is added, and the cells are cooled very slowly in a controlled-rate freezer to prevent osmotic cellular injury during ice crystal formation. HSC may be stored for years in a cryofreezer, which typically uses liquid nitrogen.

As is known in the art, hematopoietic stem and progenitor cell transplantation are often performed during the treatment of individuals following ablative radiation or chemotherapy. A need for transplantation may be caused by genetic or environmental conditions, e.g. chemotherapy, exposure to radiation, etc. The cells for transplantation may be mixtures of cells, e.g. buffy coat lymphocytes from a donor, or may be partially or substantially pure. The cells may be autologous cells, particularly if removed prior to cytoreductive or other therapy, or allogeneic cells, and may be used for hematopoietic stem or progenitor cell isolation and subsequent transplantation.

Usually, at least $1 \times 10^5$ cells will be administered, preferably $1 \times 10^6$, $10^7$, $10^8$ or more. The composition may be introduced by injection, catheter, or the like. The cells may be combined with the agonist antibody prior to administration. For example, the cells may be combined with the antibody at a concentration of from about 10 µg/ml, about 100 µg/ml, about 1 mg/ml, about 10 mg/ml, etc., at a temperature of from about 4°, about 10°, about 25° about 37°, where in some embodiments the cells are maintained on ice.

In other transplantation related methods, the antibodies of the invention are provided in the context of a solid organ transplantation. As used herein, the term "solid organ transplantation" is used in accordance with the conventional meaning of the term, where an organ from a donor, which donor may be living or deceased, in placed into the body of a recipient in the appropriate position and cardiovascular connections to be physiologically integrated into the recipient. Transplantation of a kidney, pancreas including pancreatic islet cells; heart; lungs, intestine, liver, and the like as known in the art is of interest. The transplanted organ may be referenced as a "graft", and the physiological integration of the organ may be referred to as engraftment.

The antibody can be separately provided to the recipient prior to introduction of the cells or organ, concurrently with the introduction of the cells or organ, or shortly after administration of the cells or organ. The antibody may be provided at an effective dose, e.g. up to about 1 ng/kg body weight, up to about 10 ng/kg body weight, up to about 100 ng/kg body weight, up to about 1 µg/kg body weight, up to about 10 µg/kg body weight, up to about 100 µg/kg body weight. or more. The compositions are administered in any physiologically acceptable medium, normally intravascularly, although they may also be introduced into bone or other convenient site, where the cells may find an appropriate site for regeneration and differentiation.

Monoclonal antibodies or portions thereof (and compositions comprising the antibodies or portions thereof) of the invention can be administered in a variety of suitable fashions, e.g., intravenously (IV), subcutaneously (SC), or, intramuscularly (IM) to the subject. The antibody or antigen-binding portion thereof can be administered alone or in combination with another therapeutic agent, e.g., a second human monoclonal antibody or antigen binding portion thereof. In another example, the antibody is administered together with another agent, for example, an immunosuppressive agent, an erythropoiesis-stimulating agent (ESA), in combination with therapeutic cell compositions, and the like.

In some embodiments the monoclonal antibodies of the invention enhance the numbers of circulating red blood cells or other hematopoietic cells by reducing phagocytosis. Antibodies can be administered in a dose and route as described above, i.e. at an effective dose, e.g. up to about 1 ng/kg body weight, up to about 10 ng/kg body weight, up to about 100 ng/kg body weight, up to about 1 µg/kg body weight, up to about 10 µg/kg body weight, up to about 100 µg/kg body weight. or more. Dosing for such purposes may be repeated as required, e.g. daily, semi-weekly, weekly, semi-monthly, monthly, or as required during relapses.

Such methods may be combined with administration of an erythropoiesis-stimulating agent (ESA). ESAs are known in the art and include, but are not limited to erythropoietin (EPO), EPO derivatives, and EPO-stimulating compounds. Suitable examples include but are not limited to: EPO alpha, EPO beta, EPO delta, EPO omega, EPO zeta, Darbepoetin alfa (Aranesp), Epoetin alfa (Procrit), Epocept (Lupin pharma), Nanokine (Nanogen Pharmaceutical biotechnology, Vietnam), Epofit (Intas pharma), Epogen (Amgen), Epogin, Eprex, (Janssen-Cilag), NeoRecormon (Hoffmann-La Roche), Recormon, Methoxy polyethylene glycol-epoetin beta (Mircera)(Roche), Dynepo, Epomax, Silapo (Stada), Retacrit (Hospira), Epocept (Lupin Pharmaceuticals), EPOTrust (Panacea Biotec Ltd.), Erypro Safe (Biocon Ltd.), Repoitin (Serum Institute of India Limited), Vintor (Emcure Pharmaceuticals), Epofit (Intas pharma), Erykine (Intas Biopharmaceutica), Wepox (Wockhardt Biotech), Espogen (LG life sciences), ReliPoietin (Reliance Life Sciences), Shanpoietin (Shantha Biotechnics Ltd.), Zyrop Cadila (Healthcare Ltd.), EPIAO (rHuEPO), and (Shenyang Sunshine Pharmaceutical Co. LTD. China). The dose of ESA that should be administered depends on the nature of the agent that is used, and also depends on numerous subject-specific factors (e.g., age, weight, etc.). Methods of determining an appropriate dose of an ESA are known in the art. In some embodiments, the ESA is administered at a dose according to manufacturer's suggestions and in some cases may be as low as about 50 units/kg, about 100 units/kg or about 150 units/kg of body weight or as high as about 17,000 units/kg of body weight.

In other embodiments the antibodies of the invention are used in the treatment of Hemophagocytic lymphohistiocytosis (HLH) to increase the numbers of hematopoietic cells by reducing macrophage activation and phagocytosis. HLH is an uncommon disorder causing immune dysfunction in infants and young children. Many patients have an underlying immune disorder, although in some patients the underlying disorder is not known. Manifestations may include lymphadenopathy, hepatosplenomegaly, fever, and neurologic abnormalities. Diagnosis is by specific clinical and testing (genetic) criteria. Conventional treatment is usually with chemotherapy and, in refractory cases or in cases with a genetic cause, hematopoietic stem cell transplantation.

HLH can be: familial (primary), or acquired (secondary). HLH is diagnosed when patients fulfill at least 5 of the criteria described below or have a mutation in a known HLH-associated gene. Acquired HLH can be associated with other immune disorders (eg, leukemias, lymphomas, SLE, RA, polyarteritis nodosa, sarcoidosis, progressive systemic sclerosis, Sjögren syndrome, Kawasaki disease) and can occur in kidney or liver transplant recipients. Acquired HLH may be caused by those disorders or the immunosuppressive regimens used to treat them, and possibly by infections.

Common early manifestations include fever, hepatomegaly, splenomegaly, rash, lymphadenopathy, and neurologic abnormalities (eg, seizures, retinal hemorrhages, ataxia, altered consciousness or coma). Bone lesions may occur, and clinical manifestations may mimic child abuse. HLH can be diagnosed if there is a mutation in a known causative gene or if at least 5 of 8 diagnostic criteria are met: fever (peak temperature of >38.5° C. for >7 days); splenomegaly (spleen palpable >3 cm below costal margin); cytopenia involving >2 cell lines (Hb<9 g/dL, absolute neutrophil count<100/µL, platelets<100,000/µL); hypertriglyceridemia (fasting triglycerides>2.0 mmol/L or >3 standard deviations [SD] more than normal value for age) or hypofibrinogenemia (fibrinogen<1.5 g/L or >3 SD less than normal value for age); hemophagocytosis (in biopsy samples of bone marrow, spleen, or lymph nodes); low or absent natural killer cell activity; serum ferritin>500 µg/L; elevated soluble IL-2 (CD25) levels (>2400 U/mL or very high for age).

In some embodiments, the present invention also provides methods for the treatment of a variety of diseases and disorders using the antibodies of the invention as an immunomodulatory agent, including but not limited to immunosuppressive agents, alone or in combination with another agent effective in treating disease.

Due to their role in phagocytosis, macrophages are involved in many diseases of the immune system. For example, they participate in the formation of granulomas, which are inflammatory lesions that are caused by a large number of diseases. Some disorders of ineffective phagocytosis and macrophage function have been described. Macrophages are the predominant cells involved in creating the progressive plaque lesions of atherosclerosis (Lucas A D, Greaves D R Expert Rev Mol Med 3 (25): 1-18). Several non-limiting examples of macrophage related diseases are described below.

In one embodiment, macrophage related diseases are diseases characterized by activated macrophages. The macrophages may be chronically activated or acutely activated, or both. While not wishing to be bound by theory, treatments according to certain embodiments of the invention may interfere with the activation of monocytes to macrophages, or may increase deactivation of macrophages, or both.

Macrophage related diseases that can be treated or prevented by the administering antibodies of the invention in an effective dose for treatment of cancer, autoimmune diseases such as multiple sclerosis and rheumatoid arthritis, macrophage activation syndrome, atherosclerosis, diabetes mellitus, Kawasaki disease, asthma, sarcoidosis, periodontitis, Whipple's disease, pulmonary alveolar proteinosis, macrophage related pulmonary disease, Leishmaniasis, obesity complications, hemodialysis related inflammation, microbial infection, retroviral infection such as HIV infection, and inflammation. In addition, for many of the diseases, although macrophages may not be the primary trigger of the disease, their involvement is evident in the disease related complications or secondary manifestations. Such macrophage related complications can be treated or prevented by the methods of the present invention. For example, macrophages contribute to neurological signs in acquired immunodeficiency syndrome (AIDS) and non-AIDS-related diseases. Other examples of complications that may involve macrophages and can be treated with the subject methods include but are not limited to transplant-related complications as described above, acute atheroma complication, metabolic syndrome, hypertension, obesity, diabetic complications (nephropathy, neuropathy and retinopathy), complications of the tobacco-related disease, liver complications, inflammatory neurological diseases, and a variety of other disorders.

In one embodiment, the disease to be treated shows upregulation of differentiation of monocytes to activated macrophages, where treatment according to the invention reduces such upregulation. The reduction in upregulation may in some embodiments occur before upregulation, or alternatively, by downregulation after the fact, or both.

Macrophage-activation syndrome (MAS) is a severe, potentially life-threatening, complication of several chronic rheumatic diseases of childhood, and can be treated by administration of an effective dose of antibodies of the present invention. It occurs most commonly with systemic-onset juvenile idiopathic arthritis (SoJIA), which is also known as Still's disease. In addition, MAS has been described in association with diseases including but not limited to systemic lupus erythematosus (SLE), Kawasaki disease, and adult-onset Still's disease. It is thought to be closely related and pathophysiologically very similar to reactive (secondary) hemophagocytic lymphohistiocytosis (HLH). The hallmark clinical and laboratory features include high fever, hepatosplenomegaly, lymphadenopathy, pancytopenia, liver dysfunction, disseminated intravascular coagulation, hypofibrinogenemia, hyperferritinemia, and hypertriglyceridemia. Despite marked systemic inflammation, the erythrocyte sedimentation rate (ESR) is paradoxically depressed, caused by low fibrinogen levels. A bone marrow biopsy or aspirate usually shows hemophagocytosis. There is uncontrolled activation and proliferation of macrophages and T lymphocytes, with a marked increase in circulating cytokines, such as IFN-gamma, and granulocyte-macrophage colony-stimulating factor (GM-CSF). In many cases of MAS, decreased natural killer cell (NK-cell) function is observed. Most commonly used treatments include high-dose glucocorticoids, and cyclosporine. In refractory cases treatment regimens are used similar to that in HLH (Pinto L, et al. J Assoc Physicians India. 2007 55:185-7).

Autoimmunity is the failure of an organism to recognize its own constituent parts as self, which allows an immune response against its own cells and tissues, and can be treated by administration of an effective dose of antibodies of the present invention. Diseases that results from such aberrant immune response can be considered autoimmune diseases. Prominent examples include Coeliac disease, diabetes mellitus type 1 (IDDM), systemic lupus erythematosus (SLE), Sjogren's syndrome, Churg-Strauss Syndrome, Hashimoto's thyroiditis, Graves' disease, idiopathic thrombocytopenic purpura, and rheumatoid arthritis (RA). The treatment of autoimmune diseases is typically immunosuppressive, anti-inflammatory, or palliative. Hormone levels have been shown to affect the severity of some autoimmune diseases such as multiple sclerosis. Other causes may include the presence of fetal cells in the maternal bloodstream, i.e., microchimerism, and infections with some viruses and bacteria. The autoimmune diseases that can be treated with the methods of the present invention include but are not limited to acute disseminated encephalomyelitis, Addison's disease, alopecia areata, ankylosing spondylitis, antiphospholipid antibody syndrome, autoimmune hemolytic anemia, autoimmune hepatitis, Bullous pemphigoid, Coeliac disease, Crohns disease, dermatomyositis, diabetes mellitus type 1, Goodpasture's syndrome, Graves' disease, Guillain-Barre syndrome, Hashimoto's disease, Idiopathic thrombocytopenic purpura, Lupus erythematosus, Mixed Connective Tissue Disease, multiple sclerosis, myasthenia gravis, narcolepsy, Pemphigus vulgaris, Pernicious anemia, Polymyositis, Primary biliary cirrhosis, Rheumatoid arthritis, Sjogren's syndrome, Temporal arteritis, Ulcerative Colitis, Vasculitis, and Wegener's granulomatosis.

The monoclonal antibodies of the invention may be used in vitro in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The monoclonal antibodies of the invention can be bound to many different carriers and used to detect the presence of SIRPα. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibodies of the invention, or will be able to ascertain such, using routine experimentation. Furthermore, the binding of these labels to the monoclonal antibodies of the invention can be done using standard techniques common to those of ordinary skill in the art.

For purposes of the invention, SIRPα may be detected by the monoclonal antibodies of the invention when present in biological fluids and tissues. Any sample containing a detectable amount of SIRPα can be used. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis.

Another labeling technique which may result in greater sensitivity consists of coupling the antibodies to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies.

As a matter of convenience, the antibody of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Polynucleotides

The invention also provides isolated nucleic acids encoding the anti-SIRPα antibodies, vectors and host cells comprising the nucleic acid, and recombinant techniques for the production of the antibody. Exemplary polynucleotides encode the heavy or light chain variable region sequences set forth herein, e.g. SEQ ID NO:1 and SEQ ID NO:2.

Nucleic acids of interest may be at least about 80% identical to a sequence that encodes SEQ ID NO:1 and SEQ ID NO:2, at least about 85%, at least about 90%, at least about 95%, at least about 99%, or identical. In some embodiments a contiguous nucleotide sequence is at least about 20 nt., at least about 25 nt, at least about 50 nt., at least about 75 nt., at least about 100 nt, and up to the complete coding sequence may be used. Such contiguous sequences may encode a CDR sequence, for example as set forth in SEQ ID NO:3-8, or may encode a complete variable region. As is known in the art, a variable region sequence may be fused to any appropriate constant region sequence.

For recombinant production of the antibody, the nucleic acid encoding it is inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

The anti-SIRPα antibody of this invention may be produced recombinantly not only directly, but also as a fusion polypeptide with a heterologous or homologous polypeptide, which include a signal sequence or other polypeptide having a specific cleavage site at the N-terminus of the mature protein or polypeptide, an immunoglobulin constant region sequence, and the like. A heterologous signal sequence selected preferably may be one that is recognized and processed (i.e., cleaved by a signal peptidase) by the host cell. For prokaryotic host cells that do not recognize and process the native antibody signal sequence, the signal sequence is substituted by a prokaryotic signal sequence selected.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

Suitable host cells for cloning or expressing the DNA are the prokaryote, yeast, or higher eukaryote cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1.982)); MRC 5 cells; FS4 cells; and a human hepatoma line (Hep G2).

Host cells are transformed with the above-described expression or cloning vectors for anti-SIRPα antibody production and cultured in conventional nutrient media modified as appropriate for inducing promoters, selecting transformants, or amplifying the genes encoding the desired sequences.

In some embodiments of the invention, the provided human antibody variable regions and/or CDR regions are used in a screening method to select for antibodies optimized for affinity, specificity, and the like. In such screening methods, random or directed mutagenesis is utilized to generate changes in the amino acid structure of the variable region or regions, where such variable regions will initially comprise one or more of the provided CDR sequences, e.g. a framework variable region comprising CDR1, CDR2, CDR3 from the heavy and light chain sequences provided in SEQ ID NO:1 and 2.

These mutated variable region sequences, which are optionally combined with a second variable region sequence, i.e. $V_H$VL, with constant regions, as a fusion protein to provide for display, etc., as known in the art. Methods for selection of antibodies with optimized specificity, affinity, etc., are known and practiced in the art, e.g. including methods described by Presta (2006) Adv Drug Deliv Rev. 58(5-6):640-56; Levin and Weiss (2006) Mol Biosyst. 2(1):49-57; Rothe et al. (2006) Expert Opin Biol Ther. 6(2):177-87; Ladner et al. (2001) Curr Opin Biotechnol. 12(4):406-10; Amstutz et al. (2001) Curr Opin Biotechnol. 12(4):400-5; Nakamura and Takeo (1998) J Chromatogr B Biomed Sci Appl. 715(1):125-36 each herein specifically incorporated by reference for teaching methods of mutagenesis selection. Such methods are exemplified by Wu et al. (2005) J. Mol. Biol. (2005) 350, 126-144.

Such screening methods may involve mutagenizing a variable region sequence comprising one or more CDR sequences set forth herein; expressing the mutagenized sequence to provide a polypeptide product; contacting the polypeptide with an SIRPα antigen; identifying those polypeptide having the desired antigen affinity or specificity.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl) benzene allow for faster flow rates and shorter processing times than can be achieved with agarose. Where the antibody comprises a $CH_3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Formulations

The antibody formulations of the present invention may be used to treat the various conditions as described herein. The antibody formulation is administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the antibody formulation is suitably administered by pulse infusion, particularly with declining doses of the antibody.

For the prevention or treatment of disease, the appropriate dosage of antibody will depend on the type of disease to be treated, the severity and course of the disease, whether the antibody is administered for preventive purposes, previous therapy, the patient's clinical history and response to the antibody, and the discretion of the attending physician. The antibody is suitably administered to the patient at one time or over a series of treatments.

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is one or more antibodies in a formulation of the invention as described above. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

Therapeutic formulations comprising one or more antibodies of the invention are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to reduce virus titer in an infected individual.

The therapeutic dose may be at least about 0.01 µg/kg body weight, at least about 0.05 µg/kg body weight; at least about 0.1 µg/kg body weight, at least about 0.5 µg/kg body weight, at least about 1 µg/kg body weight, at least about 2.5 µg/kg body weight, at least about 5 µg/kg body weight, and not more than about 100 µg/kg body weight. It will be understood by one of skill in the art that such guidelines will be adjusted for the molecular weight of the active agent, e.g. in the use of antibody fragments, or in the use of antibody conjugates. The dosage may also be varied for localized administration, or for systemic administration, e.g. i.m., i.p., i.v., and the like.

The antibody need not be, but is optionally formulated with one or more agents currently used to prevent or treat the disease of interest. These are generally used in the same dosages and with administration routes as used hereinbefore or about from 1 to 99% of the heretofore employed dosages.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The formulation herein may also contain more than one active compound as necessary for the particular indication being treated, preferably those with complementary activities that do not adversely affect each other. For example, it may be desirable to further provide an antiviral agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

A pharmaceutically effective dose is that dose required to prevent, inhibit the occurrence, or treat (alleviate a symptom at least to some extent) of a disease state, e.g. to reduce virus titer in an infected individual. The pharmaceutically effective dose depends on the type of disease, the composition used, the route of administration, the type of subject being treated, subject-dependent characteristics under consideration, concurrent medication, and other factors that those skilled in the medical arts will recognize. Generally, an amount between 0.1 mg/kg and 100 mg/kg body weight/day of active ingredients is administered.

Formulations and methods of delivery of agents to the liver are known in the art, see, e.g., Wen et al., 2004, *World J. Gastroenterol.* 10:244-9; Murao et al., 2002, *Pharm. Res.* 19:1808-14; Liu et al., 2003, *Gene Ther.* 10:180-7; Hong et al., 2003, *J. Pharm. Pharmacol.* 54; 51-8; Herrmann et al., 2004, *Arch. Virol.* 149:1611-7; and Matsuno et al., 2003, *Gene. Ther.* 10:1559-66.

Formulations and methods of delivery of agents to the skin or mucosa are known in the art. Such delivery systems include, e.g., aqueous and nonaqueous gels, creams, multiple emulsions, microemulsions, liposomes, ointments, aqueous and nonaqueous solutions, lotions, patches, suppositories, and tablets, and can contain excipients such as solubilizers, permeation enhancers (e.g., fatty acids, fatty acid esters, fatty alcohols and amino acids), and hydrophilic polymers (e.g., polycarbophil and polyvinylpyrolidone).

Oral administration can be accomplished using pharmaceutical compositions containing an agent of interest formulated as tablets, lozenges, aqueous or oily suspensions, dispersible powders or granules, emulsion, hard or soft capsules, or syrups or elixirs. Such oral compositions can contain one or more such sweetening agents, flavoring agents, coloring agents or preservative agents in order to provide pharmaceutically elegant and palatable preparations. Tablets, which can be coated or uncoated, can be formulated to contain the active ingredient in admixture with non-toxic pharmaceutically acceptable excipients, e.g., inert diluents; such as calcium carbonate, sodium carbonate, lactose, calcium phosphate or sodium phosphate; granulating and disintegrating agents, for example, corn starch, or alginic acid; binding agents, e.g., starch, gelatin or acacia; and lubricating agents, for example magnesium stearate, stearic acid or talc. Where a coating is used, the coating delay disintegration and absorption in the gastrointestinal tract and thereby provide a sustained action over a longer period.

Where the formulation is an aqueous suspension, such can contain the active agent in a mixture with a suitable excipient(s). Such excipients can be, as appropriate, suspending agents (e.g., sodium carboxymethylcellulose, methylcellulose, hydropropyl-methylcellulose, sodium alginate, polyvinylpyrrolidone, gum tragacanth and gum acacia); dispersing or wetting agents; preservatives; coloring agents; and/or flavoring agents.

Suppositories, e.g., for rectal administration of agents, can be prepared by mixing the agent with a suitable non-irritating excipient that is solid at ordinary temperatures but liquid at the rectal temperature and will therefore melt in the rectum to release the drug. Such materials include cocoa butter and polyethylene glycols.

Dosage levels can be readily determined by the ordinarily skilled clinician, and can be modified as required, e.g., as required to modify a subject's response to therapy. In general dosage levels are on the order of from about 0.1 mg to about 140 mg per kilogram of body weight per day. The amount of active ingredient that can be combined with the carrier materials to produce a single dosage form varies depending upon the host treated and the particular mode of administration. Dosage unit forms generally contain between from about 1 mg to about 500 mg of an active ingredient.

The invention now being fully described, it will be apparent to one of ordinary skill in the art that various changes and modifications can be made without departing from the spirit or scope of the invention.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Example 1

The P362 antibody was selected for binding to SIRPα from a library of human V-regions reformatted into scFv's (from Feldhaus et al., Nature Biotech 2003).

Figure 1A:
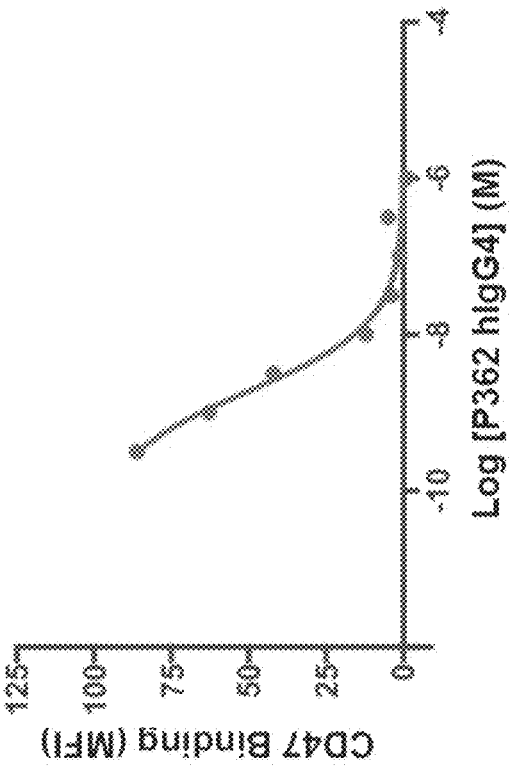

As shown in FIG. 1, varying concentrations of P362 antibody were added to yeast expressing human SIRPα, in the presence of a fixed concentration of wild type human CD47 labeled with Alexa Fluor 647. As the concentration of P362 increased, binding of CD47 to SIRPα was increasingly inhibited. Varying concentrations of P362 labeled with Alexa Fluor 647 were added to primary human macrophages.

Figure 2:
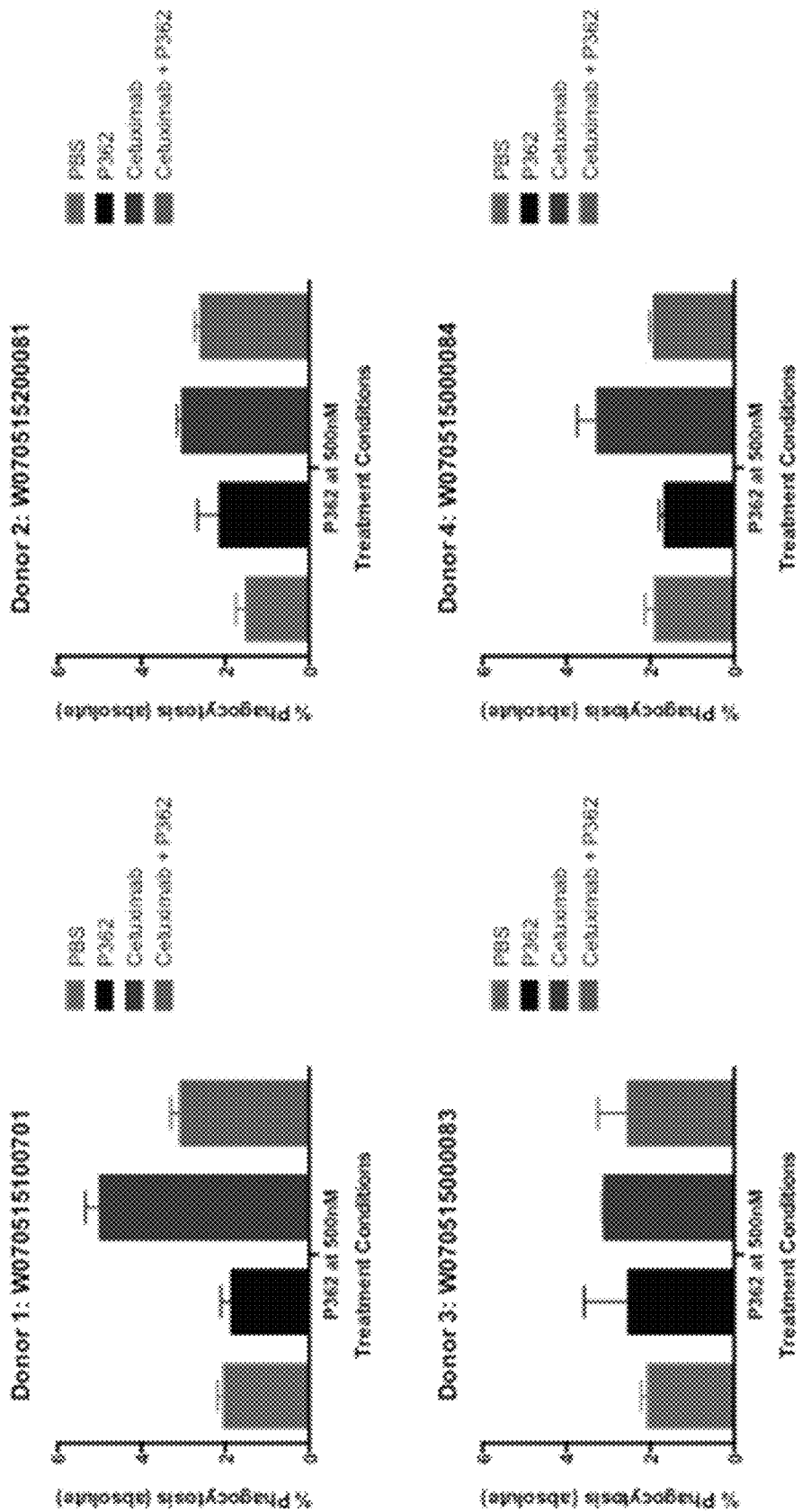
FIG. 2. Inhibition of Macrophage Mediated Phagocytosis by Anti-SIRPα Agonist Antibody P362A. P362 hIgG4 significantly decreased the phagocytosis of a colorectal adenocarcinoma cell line by primary human macrophages when opsonized by cetuximab.

Shown in FIG. 2, in each reaction, 50,000 primary human macrophages were added to 100,000 GFP+ DLD-1 cells, a colorectal adenocarcinoma cell line, and cells were incubated together for 2 hours at 37 C under the following treatment conditions: PBS, P362, cetuximab, and cetuximab with P362. Macrophages were then stained with an APC-conjugated anti-CD45 antibody. The reactions were analyzed using FACS, and "% phagocytosis" indicated the percent of GFP+ macrophages. Primary macrophages from 4 donors were used, and reactions were performed in triplicates.

Figures 3A, 3B:
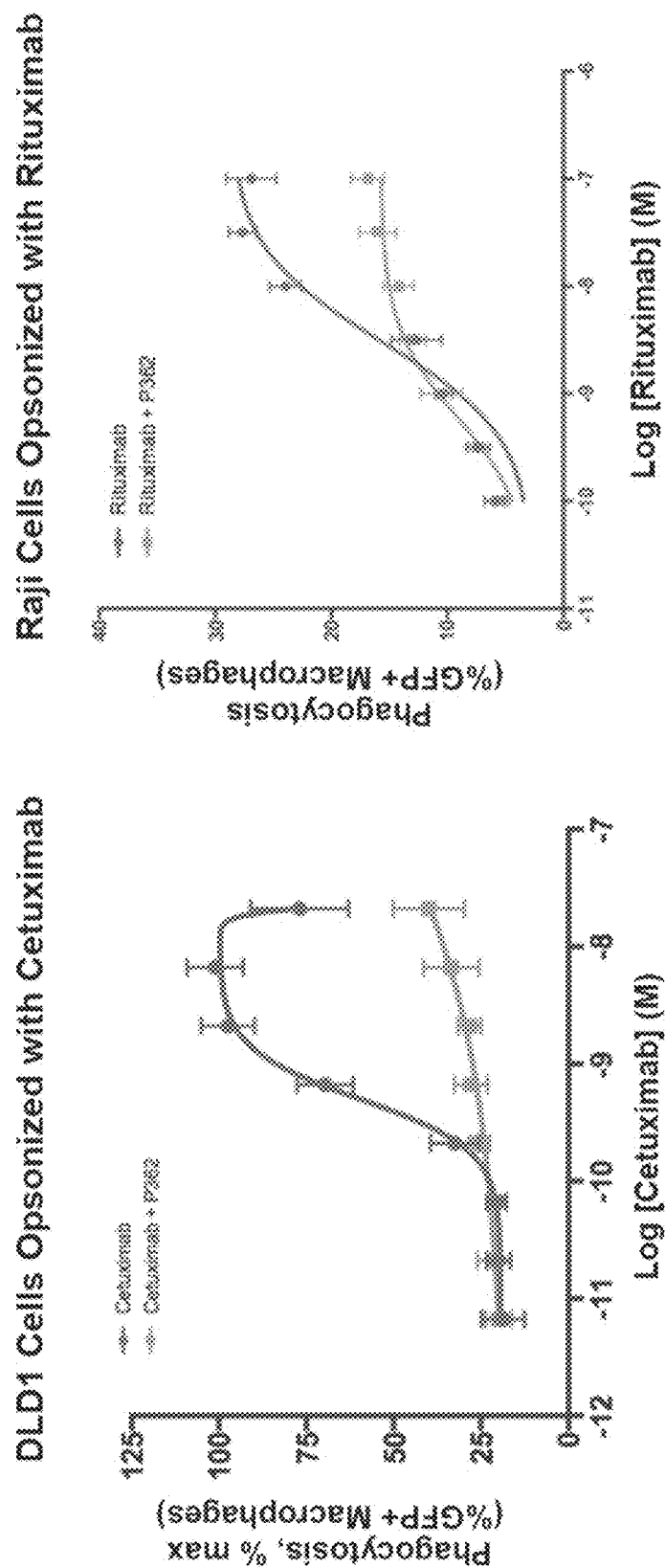
FIG. 3A-3B. Inhibition of Phagocytosis of Opsonized Cells. Dose response curves of phagocytosis where increasing concentrations of a monoclonal antibody was titrated with and without a fixed concentration of P362 hIgG4.

Using the same assays as described for FIG. 2, varying concentrations of cetuximab were added to in vitro phagocytosis assays in the presence of a constant concentration of P362, using the same DLD-1 colorectal adenocarcinoma cell lines, shown in FIG. 3A. Data using macrophages from 2 donors were normalized and combined. Shown in FIG. 3A, a similar assay was performed with varying concentrations of rituximab were added to in vitro phagocytosis assays in the presence of a constant concentration of P362. Assays were performed using Raji cells, a Burkitt's lymphoma cell line. Data using macrophages from 2 donors were normalized and combined.

Figure 4:
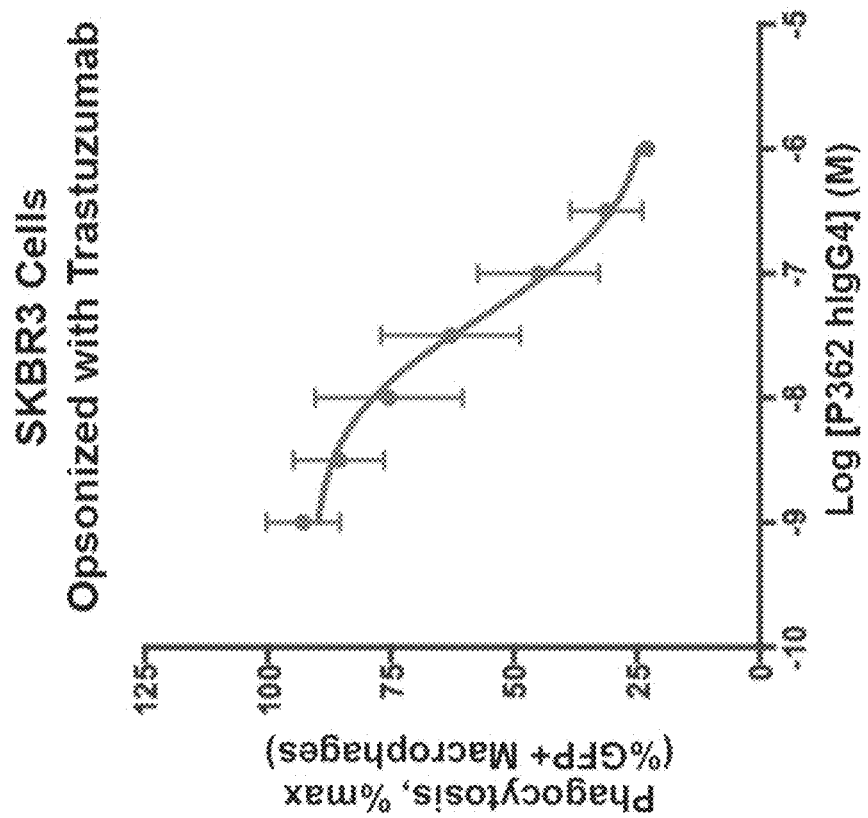
FIG. 4. Inhibition of Phagocytosis of Opsonized Cells. Dose response curve of phagocytosis, where increasing concentrations of P362 hIgG4 was titrated in the presence of a fixed dose of trastuzumab. P362 hIgG4 significantly decreased the efficacy of trastuzumab-induced phagocytosis of SKBR3 breast cancer cells.

Shown in FIG. 4, Varying concentrations of P362 were added to in vitro phagocytosis assays in the presence of a fixed concentration of trastuzumab. Assays were performed as described in FIG. 2, except using SKBR3 cells, a breast adenocarcinoma cell line. Data using macrophages from 2 donors were normalized and combined.

Figure 5:
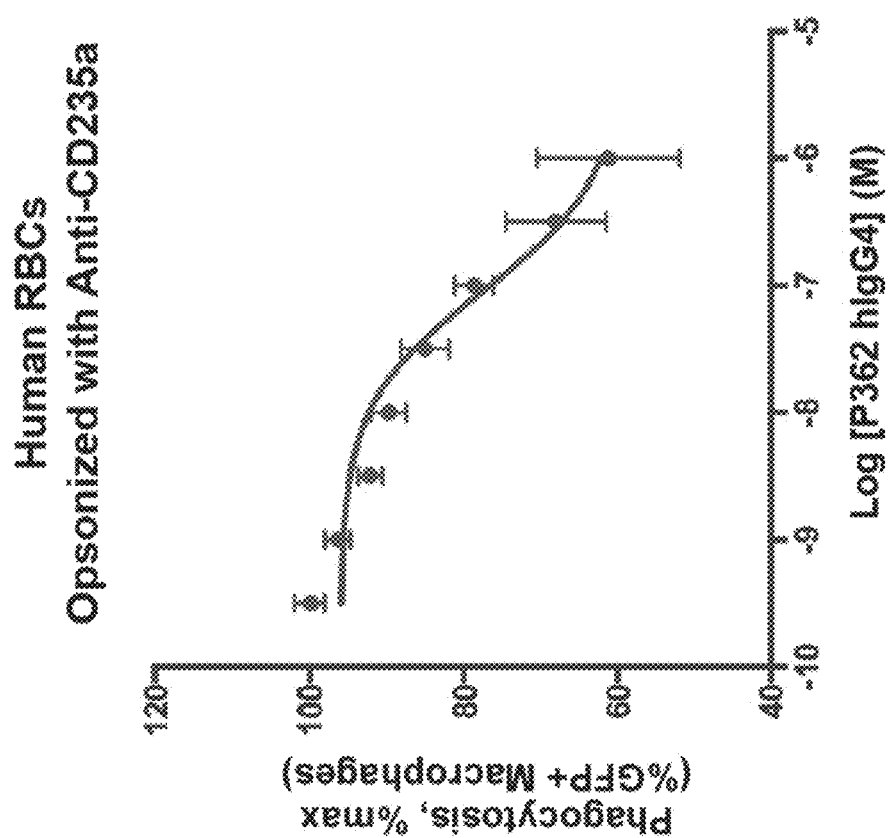

Varying concentrations of P362 were added to in vitro phagocytosis assays in the presence of a fixed concentration of anti-CD235a, shown in FIG. 5. Assays were performed as described in FIG. 2, except using human red blood cells, labeled with CFSE. Data using macrophages from 2 donors were normalized and combined.

Figure 6:
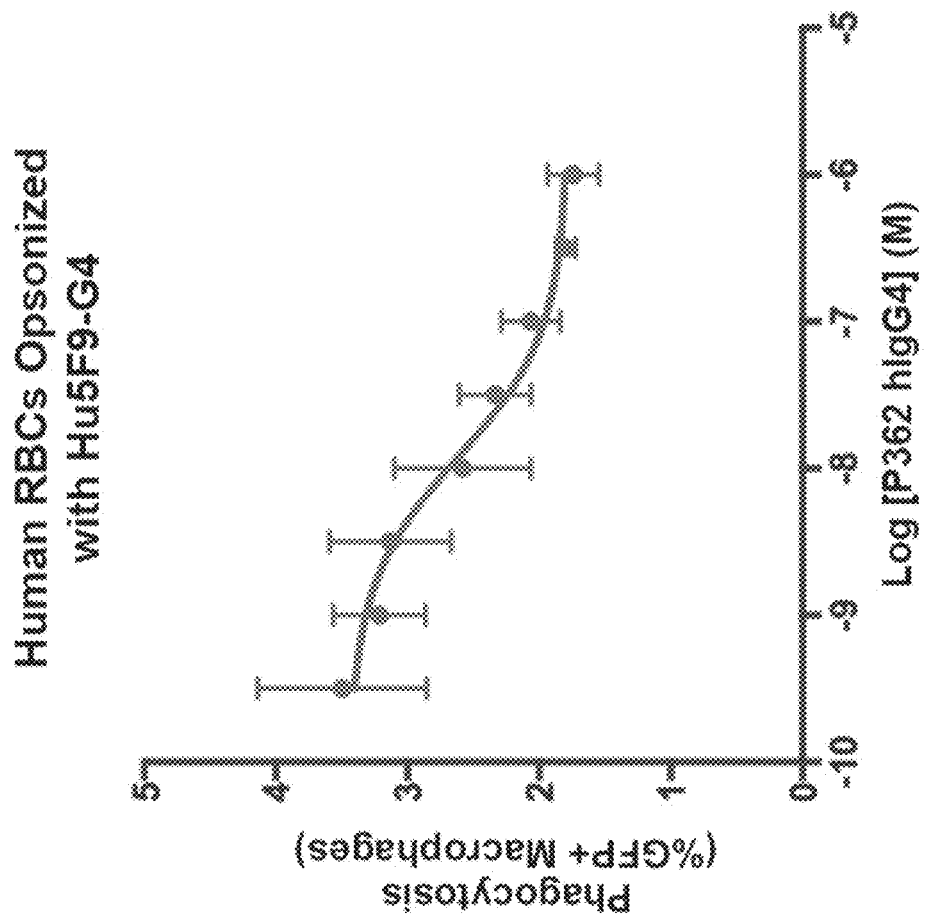
FIG. 6. P362 Protects Against Anti-CD47 Mediated Erythrophagocytosis. Dose response curve of phagocytosis of RBCs, where increasing concentrations of P362 hIgG4 was titrated in the presence of a fixed dose of Hu5F9-G4. P362 hIgG4 significantly reduced the erythrophagocytosis of RBCs caused by Hu5F9-G4.

Varying concentrations of P362 were added to in vitro phagocytosis assays in the presence of a fixed concentration of Hu5F9-G4, and anti-CD47 antibody, shown in FIG. 6. Assays were performed as described in FIG. 2, except using human red blood cells, labeled with CFSE. Data using macrophages from 2 donors were normalized and combined.

Figure 7:
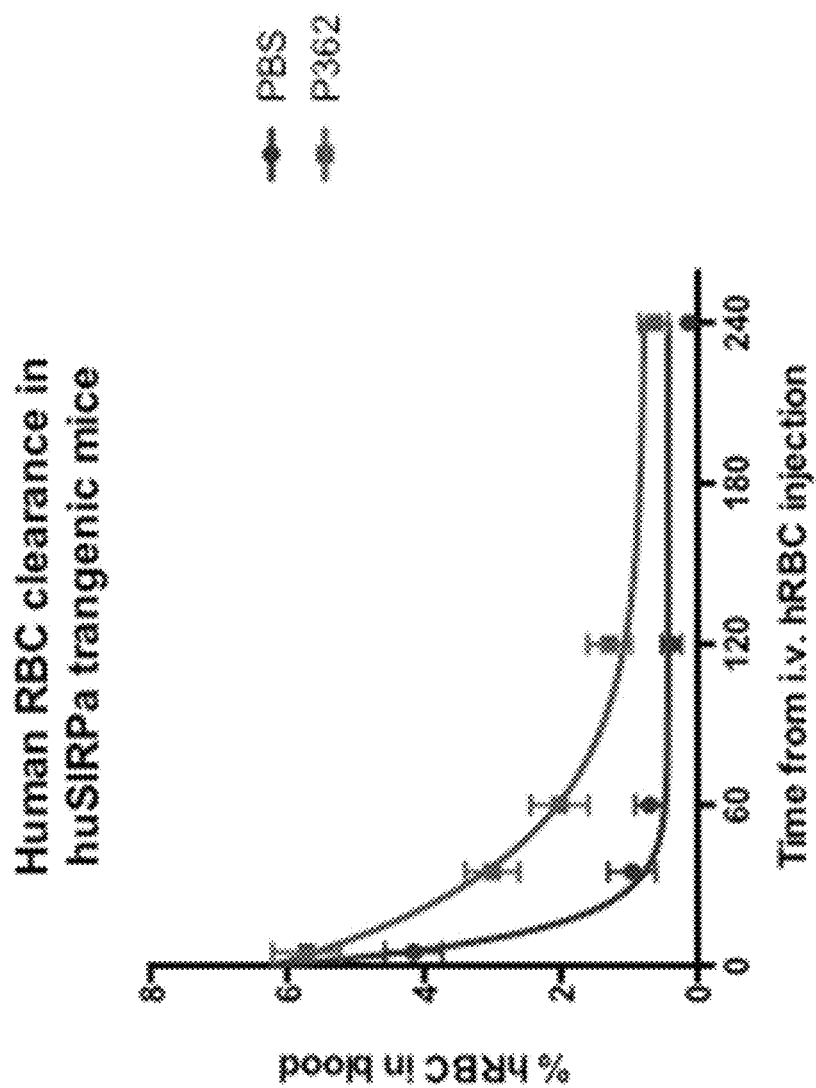
FIG. 7. P362 increases the half-life of human RBCs injected into transgenic mice.

Shown in FIG. 7, two cohorts, each with five transgenic human SIRPα mice, were pretreated with either PBS or 250 ug P362. After 24 hours, human red blood cells (RBCs) were labeled with CFSE, and 150 million RBCs were injected per mouse via tail vein. After injection, blood was collected at 5, 35, 60, 120, and 240 minutes. The plot shows the percent of RBCs remaining in blood that were CFSE positive versus time from injection. P362 increased the half-life of human RBCs in these transgenic mice from 8.6 seconds (PBS group) to 28.6 seconds.

What is claimed is:

1. An isolated monoclonal antibody or fragment thereof that selectively binds to human SIRPα wherein the antibody comprises two variable regions, wherein one variable region comprises the CDR sequences set forth in SEQ ID NO:3, 4 and 5; and the other variable region comprises the CDR sequences set forth in SEQ ID NO:6, 7 and 8.

2. The antibody of claim 1, wherein the antibody is a human monoclonal antibody.

3. The antibody or fragment of claim 1, wherein the antibody is a variable region fragment.

4. The antibody or fragment of claim 1, wherein the variable regions are present on a single polypeptide chain.

5. The antibody or fragment of claim 1, wherein the variable regions are present on separate polypeptide chains.

6. The antibody of claim 5, wherein the separate polypeptide chains are, respectively, a heavy chain and a light chain.

7. The antibody of claim 1, comprising a heavy and light chain variable region sequence as set forth in SEQ ID NO:1 and SEQ ID NO:2.

* * * * *

SEQUENCE LISTING

```
<160> NUMBER OF SEQ ID NOS: 8

<210> SEQ ID NO 1
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 1

Gln Val Gln Leu Val Glu Ser Glu Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

Glu Met Asn Trp Val Arg Gln Ala Pro Gly Lys Gly Leu Glu Trp Val
            35                  40                  45

Ser Tyr Ile Ser Ser Gly Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Ala Lys Gly Tyr Tyr Tyr Gly Met Asp Val Trp Gly Gln
            100                 105                 110

Gly Thr Thr Val Thr Val Ser Ser
            115                 120

<210> SEQ ID NO 2
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 2

Gln Pro Val Leu Thr Gln Ser Pro Ser Val Ser Val Ser Pro Gly Gln
 1               5                  10                  15

Thr Ala Ser Ile Thr Cys Ser Gly Asp Lys Leu Gly Asp Thr Tyr Ala
             20                  25                  30

Cys Trp Tyr Gln Gln Lys Pro Gly Gln Ser Pro Val Leu Val Ile Tyr
             35                  40                  45

Gln Asp Thr Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr Val Val
                 85                  90                  95

Phe Gly Gly Gly Thr Lys Leu Thr Val Leu
            100                 105

<210> SEQ ID NO 3
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 3

Phe Thr Phe Ser Ser Tyr Glu Met Asn
 1               5

<210> SEQ ID NO 4
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 4

Trp Val Ser Tyr Ile Ser Ser Ser Gly Ser Thr Ile Tyr Tyr
 1               5                  10

<210> SEQ ID NO 5
<211> LENGTH: 12

```
<212> TYPE: PRT
<213> ORGANISM: Artificial sequence
<220> FEATURE:
<223> OTHER INFORMATION: Synthetic polypeptide

<400> SEQUENCE: 5

Arg Glu Ala Lys Gly Tyr Tyr Tyr Gly Met Asp Val
1               5                   10

<210> SEQ ID NO 6
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 6

Lys Leu Gly Asp Thr Tyr Ala Cys
1               5

<210> SEQ ID NO 7
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 7

Leu Val Ile Tyr Gln Asp Thr Lys Arg Pro Ser
1               5                   10

<210> SEQ ID NO 8
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 8

Gln Ala Trp Asp Ser Ser Thr Val
1               5
```